United States Patent [19]

Berg

[11] Patent Number: 5,292,644
[45] Date of Patent: Mar. 8, 1994

[54] RAPID PROCESS FOR DETECTION COLIFORM BACTERIA

[76] Inventor: James D. Berg, Aquateam, Postboks 6593, Rodelokka, 0501 Oslo 5, Norway

[21] Appl. No.: 653,869

[22] Filed: Feb. 8, 1991

Related U.S. Application Data

[63] Continuation of Ser. No. 117,481, Nov. 5, 1987, abandoned.

[51] Int. Cl.$^5$ .......................... C12Q 1/02; C12Q 1/04; C12M 1/16; C12N 1/20
[52] U.S. Cl. ........................................... 435/29; 435/4; 435/34; 435/38; 435/39; 435/182; 435/207; 435/244; 435/252.8; 435/299; 435/848; 435/849
[58] Field of Search .................... 435/29, 4, 18, 19, 31, 435/34, 38, 39, 182, 207, 220, 244, 253, 299, 252.8, 848, 849

[56] References Cited

U.S. PATENT DOCUMENTS

| | | | |
|---|---|---|---|
| 3,870,601 | 3/1975 | Warren et al. | 435/34 |
| 3,928,139 | 12/1975 | Dorn | 435/34 |
| 4,070,247 | 1/1978 | Burt | 435/38 |
| 4,242,447 | 12/1980 | Findl et al. | 435/39 |
| 4,259,442 | 3/1981 | Gayral | 435/14 |
| 4,308,348 | 12/1981 | Monget | 435/38 |
| 4,591,554 | 5/1986 | Koumura et al. | 435/34 |
| 4,603,108 | 7/1986 | Bascomb | 435/19 |
| 4,693,972 | 9/1987 | Mansour et al. | 435/19 |
| 4,777,137 | 11/1988 | Lemonnier | 435/34 |
| 5,210,022 | 5/1993 | Roth et al. | 435/29 |

FOREIGN PATENT DOCUMENTS

| | | |
|---|---|---|
| 8303624 | 10/1983 | PCT Int'l Appl. . |
| 8605206 | 9/1986 | PCT Int'l Appl. . |

OTHER PUBLICATIONS

Bailey et al., *Diagnostic Microbiology*, 2nd ed., C. V. Mosby Company, St. Louis (1966), pp. 318-319.

*Primary Examiner*—Michael G. Witshyn
*Assistant Examiner*—Jane A. Williams
*Attorney, Agent, or Firm*—Dunlap Codding Lee

[57] ABSTRACT

A rapid process for detecting pathogenic microorganisms in products for human consumption comprises contacting the microorganisms with a methylumbelliferone substrate. The substrate is hydrolyzed into methylumbelliferone by an enzyme given off by the microorganisms. Hydrolysis is accelerated by sodium lauryl sulfate, which renders the microorganisms more permeable to the substrate, the enzyme, or both. The methylumbelliferone is detected by its fluorescence, either in solution or on an agar medium supporting microcolonies formed from individual microorganisms.

12 Claims, 5 Drawing Sheets

RAPID PROCESS FOR DETECTION COLIFORM BACTERIA

This application is a continuation of application Ser. No. 07/117,481, filed Nov. 5, 1987 (now abandoned).

This invention relates to processes for detecting and other deleterious microorganisms, such as coliform bacteria and heterotrophic microorganisms, and more specifically has reference to processes for such detection in products for human consumption which operate in a sufficiently rapid time as to allow treatment of the product before such consumption if needed.

It has long been recognized that the quality of products for human consumption can be significantly affected by the presence of pathogenic microorganisms. Such products include drinking water, bathing water, food, food preparation equipment, and, in general, any vector which the microorganisms may use to invade the human body. If present in sufficient numbers, such microorganisms can cause product deterioration or spoilage, disease, and significant economic loss. However, conventional processes for detecting such microorganisms in such products generally require twenty-four to seventy-two hours to complete. This elapsed time is generally too great to provide information about a decrease in product quality in time to take remedial measures.

Total coliform (TC) bacteria are those normally present in the colon or intestine of humans or animals. Fecal coliform (FC) bacteria are those TC bacteria which are generally present in the feces of humans or animals.

The two former groups (TC and FC) are indicators of sanitary quality. A process for their detection is conventionally considered to be "rapid" if it takes less than twenty-four hours to perform.

Recent development in rapid processes for use in water analyses are presented in Part 919, pp. 1031-1033, *Standard Methods for the Examination and Wastewater* (APHA, 1985). They are generally not rapid enough to detect a hygienically significant concentration of microorganisms within the ordinary work shift of eight hours.

The prior art includes processes for detecting microorganisms and quantifying the concentration thereof by detecting and quantifying the enzymes which the microorganisms give off as they metabolize. The enzyme in turn is detected and quantified by its ability to cleave certain chemicals, known as fluorogenic substrates, into products. At least one of these products, the fluorescent portion, fluoresces; that is, it emits light at one wavelength when irradiated with light of a different wavelength. The fluorogenic substrate, however, does not fluoresce. The presence of fluorescence therefore indicates the presence of bacteria. See, e.g., Findl et al, U.S. Pat. No. 4,242,447.

An example of the aforementioned fluorogenic substrates are 4-methylumbelliferone (4-MU) compounds. The 4-methylumbelliferone product fluoresces upon excitation with a light with a wavelength of about 365 nm to emit a light with a wavelength of about 465 nm. MU derivatives have been used in the prior art. Snyder et al., *Appl. Environ. Microbial.*, 51 (5): 969-977 (1986); Feng et al., *Appl. Environ. Microbiol.*, 43 (6): 1320-1329 (1982); and Koumura et al., U.S. Pat. No. 4,591,554.

"Fluorescence" can be measured by measuring the amount of fluorescence after a given incubation time, or by measuring the incubation time needed to obtain a given amount of fluorescence. Processes which do this generally take enough time for the microorganisms to multiply exponentially through several generations. There is, therefore, an exponentially larger amount of fluorescence available to be measured at the end of the incubation period, whether that period is fixed or variable.

"Fluorescence" can also be measured by frequently sampling the amount of fluorescence during the first part of the incubation period, and calculating therefrom the fluorescence velocity; that is, the time rate of change in the amount of fluorescence. Processes which do this generally do not take enough time for the microorganisms to multiply exponentially through several generations. Instead, such processes rely on the tendency of the microorganisms which are initially present to produce the same amount of enzyme during each sample period, thereby causing a linearly increasing amount of fluorescence. See Snyder et al., above.

Such rapid processes have many benefits. First, they are, by definition, more rapid than those which wait several generations. Second, their accuracy is good, for two reasons. One, they measure current activity of the initially present microorganisms, rather than having to make deductions from measurements of the activity of microorganisms several generations later. Two, they generate multiple data points, a situation which lends itself well to linear regression analysis, rather than generating the single datum produced by the slower processes. Third, the linearity of the data points (or lack of it) is an indicator of the accuracy of the measurement.

Such rapid processes have a drawback as well. The microorganisms must be concentrated enough to produce a measurable amount of fluorescence velocity in less than a generation. When further concentration is not practical, means must be found which enhance the per-organism fluorescence velocity.

It is therefore an object of the present invention to provide a process which enhances the per-organism fluorescence velocity of an enzymatic measurement of a dilute sample of pathogenic microorganisms in a product for human consumption.

It is a further object of the present invention to enhance such velocity while using 4-methylumbelliferone as the fluorescent product.

In accordance with one embodiment of the present invention, a process for assaying, in a brief period of time, a dilute concentration of living pathogenic microorganisms in a sample of product for human consumption, comprises six steps.

The first step is contacting the microorganisms of the sample with an actuating medium. The actuating medium comprises: (1) a nutrient which is capable of supporting metabolism of the microorganisms; (2) a production agent which is capable of inducing the production of an enzyme in said microorganisms when the microorganisms are metabolizing; (3) a fluorogenic substrate which is capable of reacting with the enzyme to release the fluorescent portion thereof; and (4) a permeability agent which is capable of increasing the permeability of the microorganisms to the enzyme, the fluorogenic substrate, or both.

The second step is incubating the resultant mixture in an environment which allows, during the period of incubation, metabolism of the microorganisms, production of the enzyme, contacting of the enzyme (whether inside or outside the microorganisms) with the fluorogenic substrate, and release of the fluorescent portion of the fluorogenic substrate.

The third step is irradiating, at intervals during the incubation period, the fluorescent portion with light of a wavelength sufficiently close to that of an excitation wavelength characteristic of the fluorescent portion, and sufficiently intense, as to cause the fluorescent portion to fluoresce.

The remaining steps are measuring, at such intervals, the amount of emitted fluorescent light; calculating the velocity of emitted fluorescence; and determining the concentration of microorganisms from such velocity and a preestablished velocity-to-concentration correlation schedule.

In a preferred embodiment, the sample is liquid or has been liquefied, and the actuating medium is liquid. The preferred embodiment further comprises, before the contacting step, concentrating the sample by filtering it through a filter fine enough to retain the microorganisms, the subsequent contacting step being accomplished by placing the filter in the actuating medium.

In this embodiment, the production agent comprises lactose, the fluorescent portion comprises 4-methylumbelliferone, the permeability agent comprises sodium lauryl sulfate, and the fluorescent portion is caused to fluoresce with emitted light of a wavelength of about 465 nm by being excited with light of a wavelength of about 365 nm.

When it is desired to measure coliform bacteria in a concentration of at least 60 coliforms per 100 milliters in at least 15 minutes, the enzyme comprises B-D-galactosidase, and the fluorescent substrate comprises 4-methylumbelliferone-B-D-galactoside. For total coliforms the environment comprises a temperature of about 350° C. For fecal coliforms, the environment comprises a temperature of about 41.5° C.

In accordance with a second embodiment of the present invention, a process for assaying living pathogenic microorganisms in a liquid or liquefied sample of product for human consumption i.n a concentration of at least 1 microorganism per 100 milliliters, and in a time of at least six hours, comprises five steps.

The first step is filtering the sample through a filter fine enough to retain the microorganisms. The second step is placing the filter and microorganisms against a solid or at least semi-solid substance. The substance comprises the same constituents as are comprised in the actuating medium of the first embodiment of the present invention.

The third step is incubating the substance, filter, and inicroorganisins in an environment which allows, during the period of incubation, metabolism and reproduction of the microorganisms, production of the enzyme, contacting of the enzyme (whether inside or outside the microorganisms) with the fluorogenic substrate, and release of sufficient of the fluorescent portion of the fluorogenic substrate from each single microorganism and its descendants to form a visible microcolony under fluorescent conditions.

The fourth step is irradiating the microcolonies with light of a wavelength sufficiently close to that of an excitation wavelength characteristic of the fluorescent portion, and sufficiently intense, as to cause the microcolonies to fluoresce. Finally, one simply counts the number of fluorescent microcolonies.

In a preferred embodiment an alkaline solution is added to the microcolonies at the end of the incubation period, thereby enhancing fluorescence and facilitating counting; and the substance against which the filter and microorganisms is placed comprises agar. The remainder of the preferred embodiment of this second embodiment is the same as the remainder of the preferred embodiment of the first embodiment, and detects the same microorganisms.

BRIEF DESCRIPTION OF THE DRAWINGS

The above and other important features of the present invention will be better understood from the following detailed description, made with reference to the following drawings, in which.

The present invention makes use of the enzyme activity in living microorganisms, particularly the coliform group of bacteria, to detect their presence and to quantify them. Enzymes unique to a group of microorganisms can be further used to identify the group to the exclusion of others present in the sample.

Specifically, the present invention uses enzyme activity as determined by the detection of MU-derived enzyme products to detect and quantify the coliform group of bacteria.

As noted above, the coliform group includes the total coliforms (TC) and the fecal coliforms (FC). These are considered indicators of the sanitary quality of food, water, or process equipment; that is, their presence is generally thought to indicate contamination by fecal material. The coliform group constituents possess the enzyme B-D-galactosidase. The present invention detects this enzyme by the use of 4-MU-B-D-galactoside in the presence of known selective ingredients to exclude the activity and presence of any other B-D-galactosidase positive non-coliforms. TC and FC are differentiated on the basis of temperature: TC are detected at 35° C.; and FC are detected at 41.5° C.

The general procedure for the detection of TC, or FC, activity in the present invention is as follows:

(a) the sample is concentrated by passing it through a membrane filter (0.2 um to 0.80 um pore size);

(b) the microorganisms which are retained with the filter are aseptically placed in contact with a sterile medium containing the appropriate 4-MU-substrate; and (c) the resulting fluorescence is measured and utilized as (1) the rate of production of fluorescent product in the liquid medium associated with the sample determined at regular intervals over about fifteen minutes using a fluorescence detecting meter, or (2) the direct observation by eye of fluorescent product associated with colonies resulting from growth (division) of the bacteria originally retained on the filter during the concentration step.

TC are detected in the manner described above by incubation of the sample plus 4-MU-B-D-galactoside at 35° C., whereas FC are detected by like incubation at 41.5°.

The invention is illustrated by the following examples.

EXAMPLE 1

Figure 2:
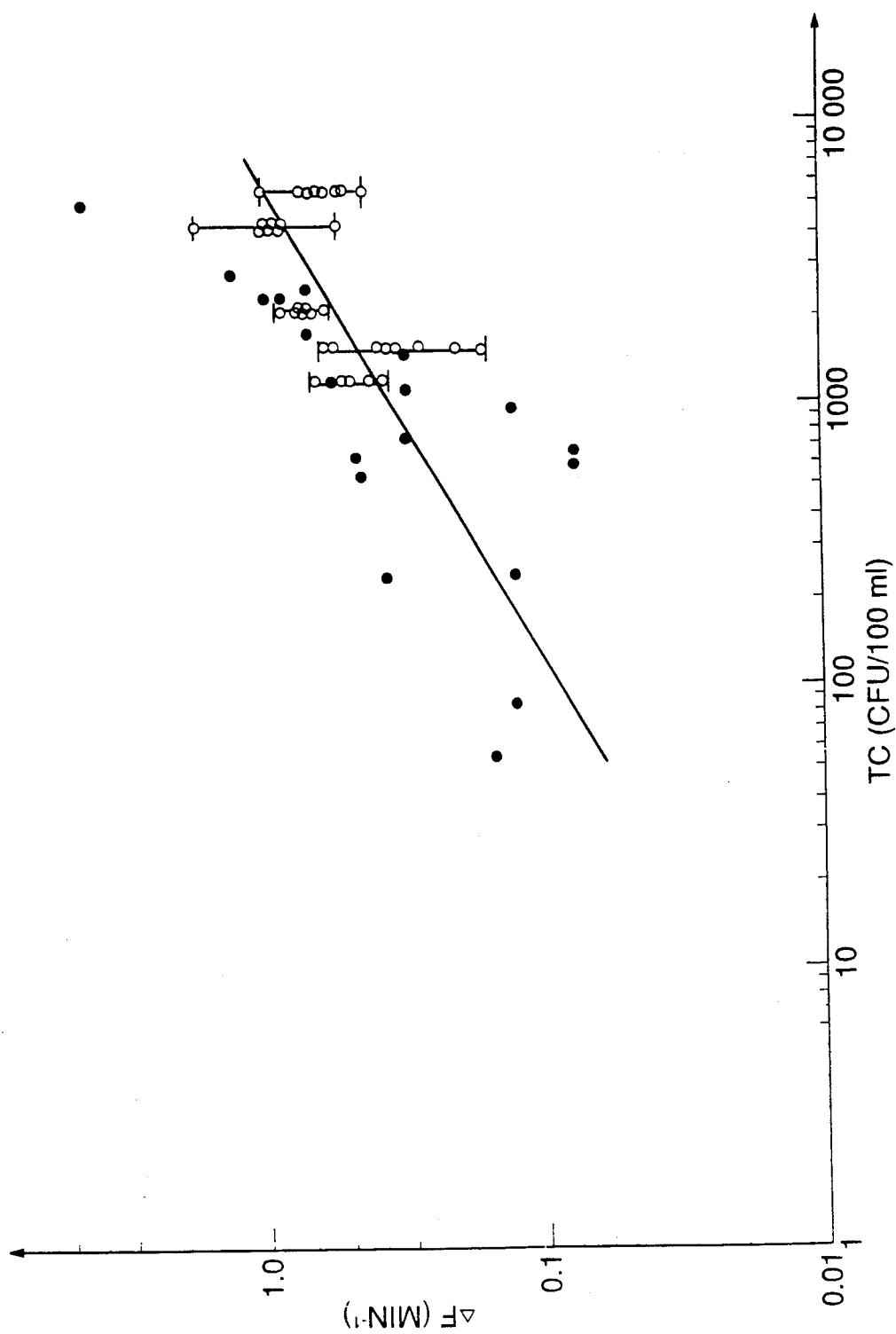
FIG. 2 is a graph correlating fluorescence velocity with total coliform concentration, with error bars indicating the range obtained when replicate samples (open circles) are incubated from one original sample.

Total coliform (TC) bacteria were analyzed in the following manner. Natural populations of coliforms were obtained from a river (Nidelven, Trondheim, Norway) receiving sewage effluent and from fresh raw domestic sewage. Samples were collected daily for experiments and diluted in tap water in varying concentrations to model drinking water with fecal coliform (FC) and nonspecific heterotrophic plate count (HPC) bacterial contamination. Concentration of coliforms ranged from 1/100 ml to 10,000/100 ml, as indicated in FIG. 2.

500 ml of a water sample were filtered through a 0.45 um pore size 47 mm diameter membrane filter (Millipore) and aseptically placed in a 250 ml flask containing 18 ml of sterile buffered actuating medium. (The 500 ml sample size was chosen as the maximum volume of surface water of turbidity <5 NTU that could be filtered in a short period of time). The medium consisted of phosphate buffered saline (PBS; pH 7.3), 0.02% sodium lauryl sulfate (Sigma Chemical Co., St. Louis, Missouri), 0.56% nutrient broth (Difco Laboratories, Detroit, Michigan), and 0.35% lactose. One of the fluorogenic substrates was added to each flask and to a sterile control flask containing the sterile medium, then placed in a shaking water bath. 4-methylumbelliferone-B-D-galactoside (4-MU-B-D-galactoside) was added at a concentration equal to 0.05 mg/ml.

The samples were incubated at 35° C. for determining TC activity, and at 41.5° C. for determining FC activity. Flasks were removed from the bath and placed in a fluorimeter (Turner Model 111) every five minutes for thirty minutes to measure the initial fluorescence velocity. The excitation and emission wavelengths for methylumbelliferone are about 365 and 465 nm using light filters 7-60 and 2A+47B respectively. Fluorescence velocity was determined by least squares linear regression.

The rapid fluorescence processes were compared with the conventional enumeration techniques described below. Heterotrophic plate count (HPC) bacteria were recovered on SPC (Difco) or R2A agar and counted after three days incubation at 20° C. Total coliform (TC) bacteria were assayed with the membrane filtration technique using M-ENDO agar (Difco) and incubated for twenty-four hours at 35° C. The seven hour and standard twenty-four hour membrane filtration processes (APHA, 1985) were used to recover fecal coliform (FC) at 41.5° C. and TC at 35° C. respectively. Peptone (0.1%) was used for all serial dilutions. All assays were done according to *Standard Methods* (APHA, 1985).

Figure 1:
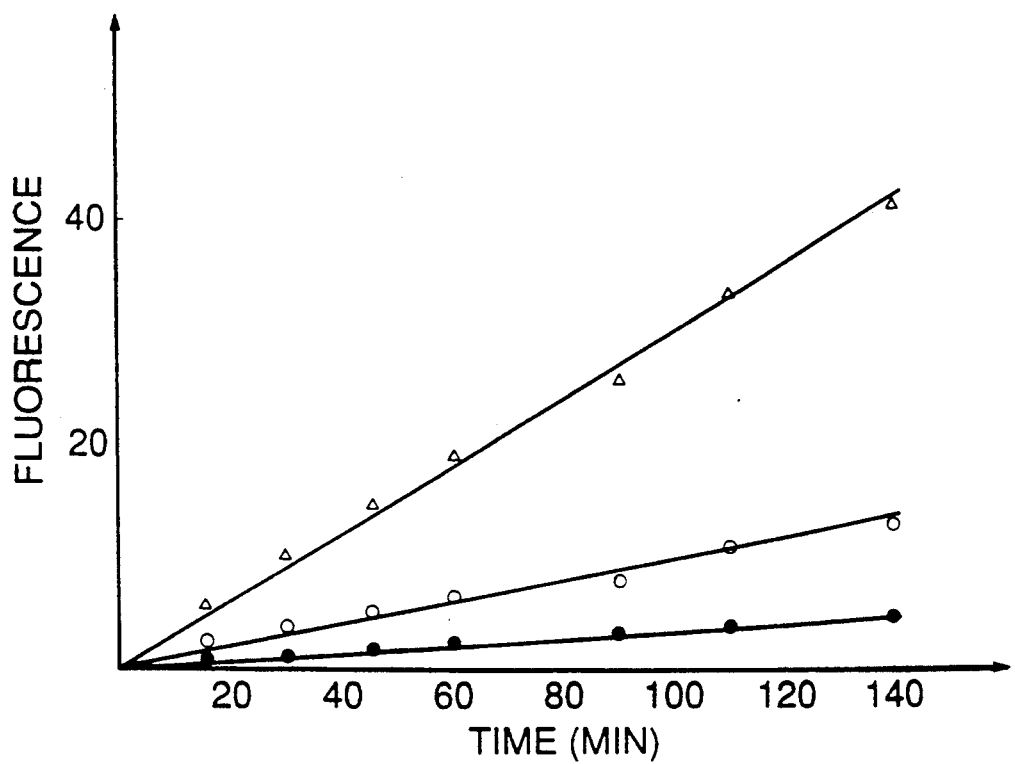
FIG. 1 is a graph showing fluorescence production by coliform bacteria in drinking water contaminated with raw sewage (solid circles), with the addition of lactose (open circles), and with the addition of sodium lauryl sulfate (triangles)

Production of methylumbelliferone from 4-MU-B-D-galactoside by coliform bacteria in drinking water contaminated with raw sewage (solid circles) is shown in FIG. 1. Addition of lactose enhanced induction of B-D-galactosidase (open circles). Addition of sodium lauryl sulfate, a common selective ingredient for coliforms, further enhanced activity (triangles). Enzyme assay temperature was 35° C.

The addition of lactose and sodium lauryl sulfate to the medium enhanced galactosidase activity. The specificity of MU-glactoside for members of the coliform group was tested by pretreating water samples with common inhibitors employed in coliform media (*Standard Methods*, 1985). Most of the activity was retained after pretreatment suggesting that the galactosidase activity was attributable to the coliform group as defined by the conditions of the assay. Replacement of sodium lauryl sulfate by the selective agents used in mT7h medium, polyethylene ether WU-1 and tergitol 7 did not enhance activity (data not shown). Linearity of the rate of product metabolism of the microorganisms; (2) a production agent which formation was generally high, $r=0.99$ for most assays. Therefore the duration of the assay in the remaining experiments was decreased from 120 minutes to 30 minutes, although 15 minutes was sufficient.

FIG. 2 shows the correlation between initial rate of hydrolysis of 4-MU-B-galactoside, as measured by initial fluorescence velocity, and the concentration of total coliform bacteria derived from raw sewage and mixed in drinking water. Enzyme assay temperature was 35° C. Error bars associated with open circles represent the range of fluorescence velocity obtained when replicate samples ($5<n<8$) are incubated from one original sample.

EXAMPLE 2

Fecal coliform (FC) bacteria were determined in the same manner as in Example 1 except that an incubation temperature equal to 41.5° C. was used.

Figure 3:
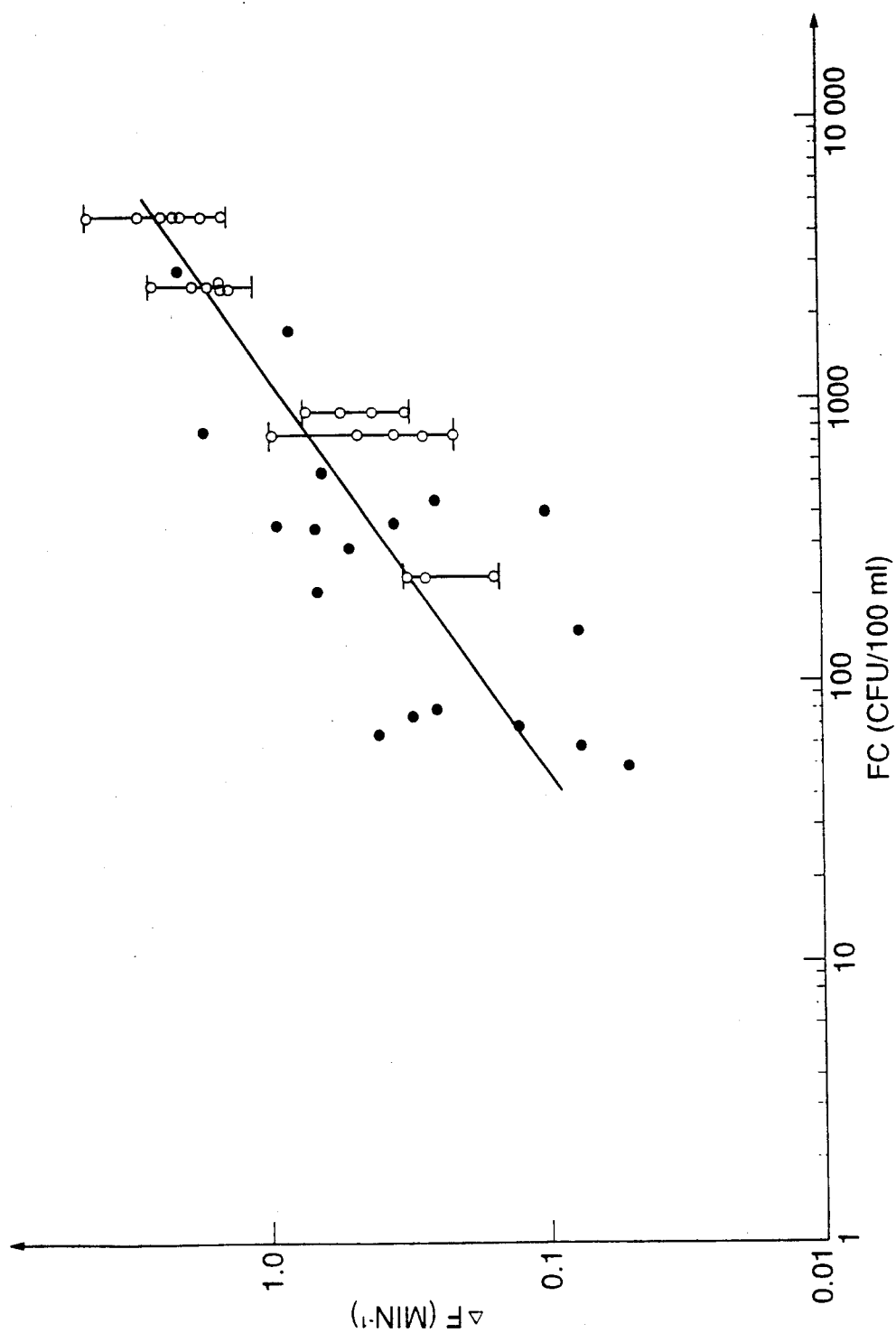
FIG. 3 is a graph similar to FIG. 2, except that it correlates fluorescence velocity with fecal coliform concentration rather than with total coliform concentration.

The results are shown in FIG. 3. Initial rate of hydrolysis of 4-MU-B-D-galactoside by fecal coliform bacteria derived from raw sewage and mixed in drinking water, as measured by initial fluorescence velocity, is compared with fecal coliform bacterial concentration. Enzyme assay temperature was 41.5° C. Error bars associated with open circles have the same meaning as in FIG. 2.

EXAMPLE 3

This example demonstrates direct counting of FC. Concentrations of FC<100/100 ml were analyzed by direct counting. Water samples were filtered and placed on a solid or at least semi-solid substance, namely M 7h FC agar (*Standard Methods*, 1985) lacking the pH indicators and d-mannitol but containing 4-MU-B-D-galactoside. Fluorescent galactosidase positive microcolonies were visible after six hours incubation at 41.5° C. with a 366 nm long wave ultraviolet light source (UVL-56, Ultraviolet Products, San Gabriel, California). The addition of 0.2 ml of an alkaline solution, namely 0.1N NAOH, after the incubation period increased the fluorescence and facilitated counting.

Figure 4:
FIG. 4 is a photograph of the agar of the second embodiment, showing individually fluorescing microcolonies.
Figure 5:
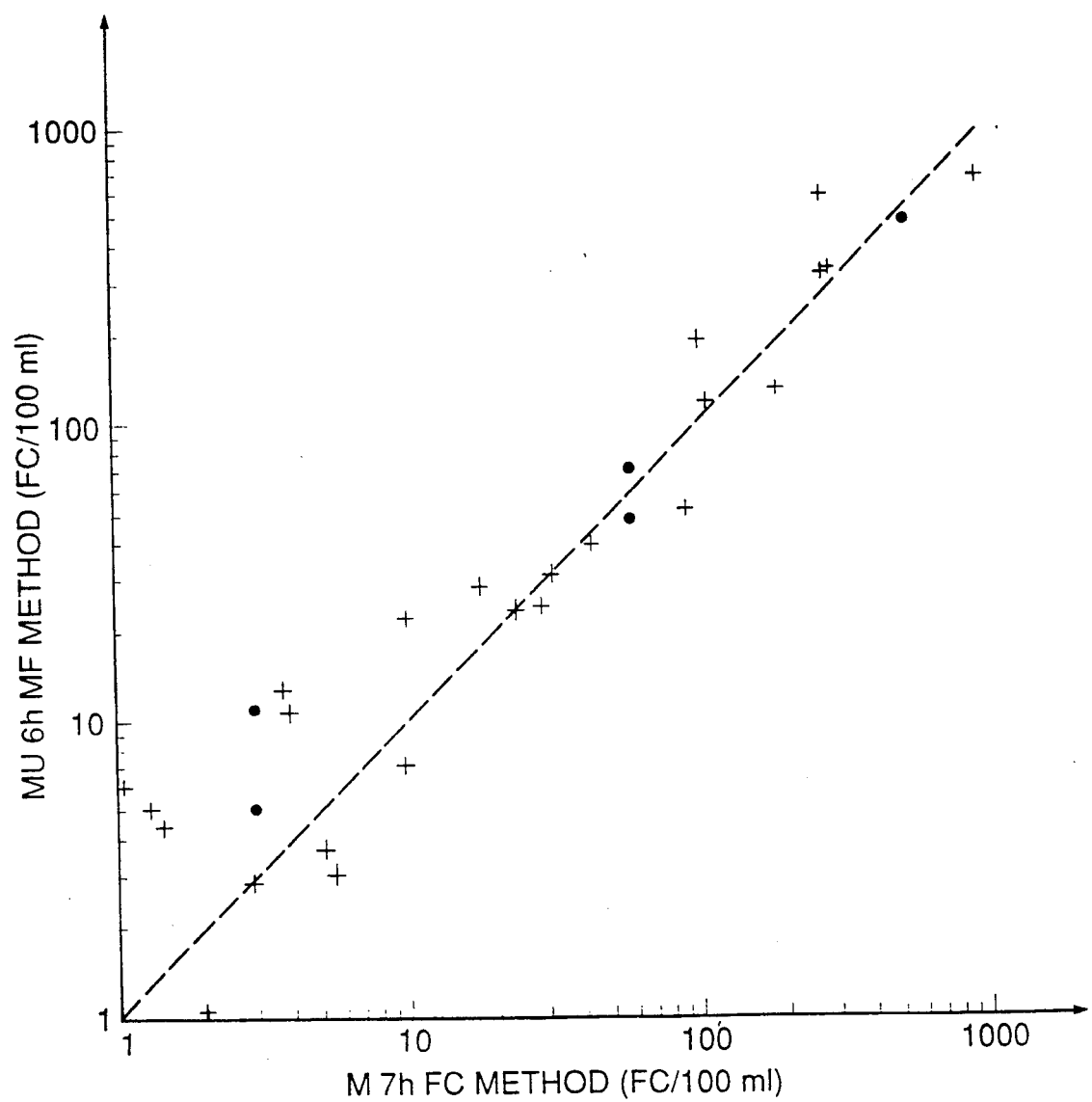
FIG. 5 is a graph correlating measurements obtained from the agar process with comparable measurements obtained from the conventional M 7h FC process.

FIG. 4 shows an example of the appearance of the microcolonies after six hours of incubation. FIG. 5 compares concentrations as measured by the agar direct counting process with concentrations measured by the conventional M 7h FC process. Pluses represent raw sewage contaminated drinking water stored at 15° C. and sampled after twenty-four to seventy-two hours for coliforms, and solid circles represent river water samples. The dashed line represents the ideal correlation, and is not fit to the data. The average ratio of MU 6h MF to M 7h FC was 1.21 to 1 for thirty-four samples.

Sixty-two fluorescing colonies randomly selected from three experiments showed 100% confirmation as FC by gas production in lauryl tryptose broth incubated at 35° C. for twenty-four hours and in EC broth incubated at 44° C. for twenty-four hours. In all experiments HPC concentrations ranged from 300/ml to 50,000/ml.

What is claimed is:

1. A rapid process for assaying a natural population of live coliform bacteria present in an original liquid or liquefied sample of product for human consumption, which may contain as well other live microorganisms, the process comprising:
   (a) collecting a known volume of the original liquid or liquefied sample;
   (b) contacting at least a portion of the known volume prior to any substantial reproduction of the coliform bacteria therein with an actuating medium thereby forming a mixture comprising:
      (1) a nutrient for supporting metabolism of the live coliform bacteria;
      (2) an amount of lactose for inducing the production of B-D-galctosidase enzyme in the live coliform bacteria while the bacteria are metabolizing;
      (3) an amount of 4-methylumbelliferone-B-D-galactoside for being acted upon by the enzyme; and,
      (4) an amount of sodium aluryl sulfate for enhancing fluorescence;
   (c) incubating the mixture for a brief period of time of less than one hour wherein occurs:
      (1) metabolism of the live coliform bacteria;
      (2) production of the enzyme;
      (3) reaction of the enzyme whether inside or outside the live coliform bacteria with the 4-methylumbelliferone-B-D-galactoside wherein is produced 4-methylumbelliferone; and,
      (4) substantially no reproduction of the live coliform bacteria;
   (d) irradiating the mixture at intervals during the incubation period with light of a wavelength sufficiently close to that of an excitation wavelength characteristic of the 4-methyl-umbelliferone and sufficiently intense as to cause the 4-methylumbelliferone to fluoresce;
   (e) measuring, at such intervals during the incubation period, the amount of emitted fluorescence;
   (f) calculating a rate of change in the amount of emitted fluoresce; and
   (g) determining the concentration of the live coliform bacteria in the original sample by comparing the rate of change of emitted fluorescence with a pre-established rate of change-to-coliform concentration correlation schedule.

2. The process of claim 1 wherein the collected known volume is less than about one liter and the step of contacting at least a portion of the known volume further comprises filtering the known volume through a filter fine enough to retain the live coliform bacteria and placing the filter in the actuating medium.

3. The process of claim 1 wherein in the step of irradiating the mixture the wavelength of light used to irradiate the mixture and 4-methylumbelliferone is about 365 nm wherein the 4-methyl- umbelliferone is caused to emit fluorescent light having a wavelength of about 465 nm.

4. The process of claim 1 wherein in the incubation step, incubation is carried out at a temperature of about 35 degrees C.

5. The process of claim 1 wherein in the incubation step incubation is carried out at a temperature of about 41.5 degrees C. wherein primarily fecal coliform bacteria are assay after the incubation process.

6. The process of claim 1 wherein in the step of incubating the mixture, the brief period of time is at least fifteen minutes.

7. A process for assaying a population of living coliform bacteria in a sample of a liquid product or liquefied product for human consumption in a concentration of at least 1 microorganism per 100 milliliters, and in a time of at least six hours, the process comprising:
   (a) filtering the samples through a filter fine enough to retain the bacteria;
   (b) placing the filter and bacteria against a solid or at least semi-solid substance comprising:
      (1) a nutrient for supporting metabolism and reproduction of the bacteria upon the filter;
      (2) an amount of lactose for inducing the production of B-D-galactosidase enzyme in the live coliform bacteria while the bacteria are metabolizing;
      (3) an amount of 4-methylumbelliferone-B-D-galactoside for reacting with the enzyme; and
      (4) an amount of sodium aluryl sulfate for enhancing fluorescence;
   (c) incubating the substance, filter, and bacteria in an environment wherein occurs, during the period of incubation:
      (1) metabolism and reproduction of the bacteria;
      (2) production of the enzyme;
      (3) reaction of the enzyme whether inside of outside the bacteria with the 4-methylumbelliferone-B-D-galactoside; and
      (4) release of sufficient of 4-methylumbelliferone from each single bacterium and its descendants to form a microcolony visible under fluorescent conditions;
   (d) irradiating the microcolonies with light of a wavelength sufficiently close to that of an excitation wavelength characteristic of 4-methylumbelliferone and sufficiently intense, as to cause the microcolonies to fluoresce; and
   (e) counting the number of fluorescent microcolonies.

8. The process of claim 1, wherein the step of incubating further comprises adding an alkaline solution to the microcolonies at the end of the incubation period whereby fluorescence is further enhanced and counting is facilitated.

9. The process of claim 7 wherein in the step of irradiating the microcolonies the wavelength of light used to irradiate the microcolonies and the 4-methyl-umbelliferone is about 365 nm wherein the 4-methylumbelliferone is caused to emit fluorescent light having a wavelength of about 465 nm.

10. The process of claim 7, wherein in the incubation step incubation is carried out at a temperature of about 35° C.

11. The process of claim 7, wherein in the incubation step incubation is carried out at a temperature of about 41.5° C. wherein primarily fecal coliform bacteria are assayed after the incubation process.

12. The process of claim 7 wherein in the step of placing the filter against a solid or semi-solid substance the substance further comprises agar.

* * * * *

UNITED STATES PATENT AND TRADEMARK OFFICE
CERTIFICATE OF CORRECTION

PATENT NO. : 5,292,644  Page 1 of 2
DATED : March 8, 1994
INVENTOR(S) : James D. Berg It is certified that error appears in the above-identified patent and that said Letters Patent is hereby corrected as shown below:

Column 1, line 2, in the title the word "DETECTION" should be --DETECTING--.

Column 1, line 7, after the word "detecting" insert --indicator microorganisms--.

Column 1, line 7, delete the word "and".

Column 1, line 8, delete the words "other deleterious microorganisms".

Column 1, line 16, after the word "pathogenic" insert --and other deleterious--.

Column 1, line 39, after the word "Examination" insert --of water--.

Column 3, line 33, delete "350°C" and insert --35°C--.

Column 6, line 15, delete "metabolism of the microorganisms".

Column 6, line 16, delete the words "(2) a production agent which".

UNITED STATES PATENT AND TRADEMARK OFFICE
CERTIFICATE OF CORRECTION

PATENT NO. : 5,292,644

DATED : March 8, 1994

INVENTOR(S) : James D. Berg

It is certified that error appears in the above-identified patent and that said Letters Patent is hereby corrected as shown below:

Column 6, line 56, delete the word "NAOH" and insert --NaOH--.

Column 7, line 29, delete the word "aluryl" and insert --lauryl--.

Column 7, line 50, delete the word "fluoresce" and insert --fluorescence--.

Column 8, line 7, delete the word "assay" and insert --assayed--.

Column 8, line 28, delete the word "aluryl" and insert --lauryl--.

Column 8, line 47, delete "1" and insert "7".

Signed and Sealed this

Nineteenth Day of July, 1994

Attest:

*Attesting Officer*

BRUCE LEHMAN

*Commissioner of Patents and Trademarks*